United States Patent [19]

Bridenne et al.

[11] Patent Number: 5,229,605

[45] Date of Patent: Jul. 20, 1993

[54] PROCESS FOR THE ELEMENTARY ANALYSIS OF A SPECIMEN BY HIGH FREQUENCY INDUCTIVELY COUPLED PLASMA MASS SPECTROMETRY AND APPARATUS FOR CARRYING OUT THIS PROCESS

[75] Inventors: Martine Bridenne, Massy; Eric Coffre, Trappes, both of France; Robert Hutton, Nantwich, Great Britain; Yves Marot, Versailles, France

[73] Assignees: L'Air Liquide, Societe Anonyme pour L'Etude et L'Exploitation des Procedes Georges Claude, Paris Cedex, France; V.G. Elemental Limited, Winsford, Great Britain

[21] Appl. No.: 815,516

[22] Filed: Jan. 2, 1992

Related U.S. Application Data

[63] Continuation of Ser. No. 636,695, Jan. 2, 1991, abandoned.

[30] Foreign Application Priority Data

Jan. 5, 1990 [FR] France .................. 90 00065

[51] Int. Cl.$^5$ .......................................... H01J 49/04
[52] U.S. Cl. ..................................... 250/282; 250/288
[58] Field of Search .................... 250/282, 288, 288 A

[56] References Cited

U.S. PATENT DOCUMENTS

| | | | |
|---|---|---|---|
| 4,760,253 | 7/1988 | Hutton | 250/288 |
| 4,804,838 | 2/1989 | Miseki | 250/288 |
| 4,933,650 | 6/1990 | Okamoto | 315/111.41 |
| 4,948,962 | 8/1990 | Mitsui | 250/288 |

FOREIGN PATENT DOCUMENTS

| | | |
|---|---|---|
| 199455 | 10/1986 | European Pat. Off. . |
| 231131 | 8/1987 | European Pat. Off. . |
| 3905303 | 8/1989 | Fed. Rep. of Germany . |
| 8912313 | 12/1989 | World Int. Prop. O. . |

OTHER PUBLICATIONS

*Analytical Chem.*, vol. 57, No. 11, Nov. 1985, pp. 2674-2679, Wash.; J. A. Olivares et al., "Ion Sampling for Inductively Coupled Plasma Mass Spectrometry", p. 2675.

*Analytical Chem.*, vol. 58, No. 1, Jan. 1986, pp. 97A-105A; R. S. Houk: "Mass Spectrometry of Inductively Coupled Plasmas".

*Analytical Chem.*, vol. 52, No. 14, Dec. 1980, pp. 2283-2289; R. S. Houk et al.: "Inductively Coupled Argon Plasma as an Ion Source for Mass Spectrophotometric Determination of Trace Elements," p. 2284, p. 2288, right column.

*Primary Examiner*—Jack I. Berman
*Attorney, Agent, or Firm*—Oblon, Spivak, McClelland, Maier & Neustadt

[57] ABSTRACT

Improvement to the process of elementary analysis of a specimen by high frequency inductively coupled plasma mass spectrometry, by means of an apparatus including a torch for producing plasma from a plasma producing medium and for injecting the specimen in this plasma and an interface for taking a sample in the specimen, comprising two consecutive conical members disposed along the same axis except that the conical members have angles with different apices and are each provided with an axial orifice enabling a fraction of the specimen to be analyzed to pass therethrough. According to the invention, a given quantity of a make-up gas is added to the specimen which is injected into the plasma, the make-up gas having a high heat producing power, so as to raise the temperature of the plasma for locally heating the sampling conical members thereby preventing the components of the specimen which are present in the plasma from depositing on the conical members. Preferably, the sampling conical members (18,19) are made of an alloy of niobium, hafnium, titanium.

6 Claims, 2 Drawing Sheets

PROCESS FOR THE ELEMENTARY ANALYSIS OF A SPECIMEN BY HIGH FREQUENCY INDUCTIVELY COUPLED PLASMA MASS SPECTROMETRY AND APPARATUS FOR CARRYING OUT THIS PROCESS

This is a continuation of application Ser. No. 07/636,695, filed on Jan. 2, 1991, now abandoned.

BACKGROUND OF INVENTION (a) Field of the Invention

The present invention relates to an improvement to the known process of analysis of a specimen of gas by means of a high frequency inductively coupled plasma, to form a source of ions sampled in a mass spectrometer and also concerns an improvement in the apparatus required for carrying out this process.

(b) Description of Prior Art

It is known that the elementary analysis of certain specimens, in particular gaseous components or those which are in solution, is more and more often required to be carried out with very precise means, in order to control the purity of these components in an extremely detailed manner. More particularly, but not exclusively, it is known that some electronic applications such as for the manufacture of highly integrated semi-conductor products, it is indispensable to produce deposits of silicon which are extremely pure and whose composition should remain strictly constant in time. Generally, such deposits are obtained from a silicon compound, such as silane, of formula $SiH_4$, which is evaporated and deposited under vacuum on a substrate. Now, the quality of the deposit obtained may be strongly modified by the presence in silane, of chemical elements such as lithium Li, sodium Na, iron Fe, calcium Ca, arsenic As, boron B, etc. . ., which modify the semi-conductive properties of the silicon deposit, sometimes substantially, even with relatively low concentrations. It will therefore be realised that it will be of interest, to be able, at any moment, to make a very precise elementary analysis of the gas or of solution used.

For this purpose, in order to achieve this result, it is well known to use a mass spectrometer which is associated with a high frequency inductively coupled plasma, this system being known in the art under the designation ICP/MS, which are the initials of the English expression "Inductively Coupled Plasma Mass Spectrometer". In particular, starting from a torch formed of a tube of quartz which receives a specimen of the gas or the solution, previously converted into a mist, to be analyzed and a plasma producing medium delivered in crown shape around the central injection portion of the specimen in the axis of the torch, the process consists in producing the plasma by means of a high frequency induction device which is coaxial to the torch, thereby producing an excitation of the gaseous mixture at the outlet of the torch and enabling to collect a flow of ions, which is then sent to a sampling device, the latter being associated with a mass spectrometer. In known manner, this device comprises two consecutive conical members which are generally made of nickel, these conical members being disposed one after the other along the axis of the torch, each being provided with an axial orifice to receive a fraction of the flow of ions to be analyzed. The first conical member, which is more opened, is called specimen conical member and is unitary with a support member which is generally cooled by a continuous circulation of an appropriate refrigerating medium, the second conical member, mounted downstream of the latter, being designated under the term sampling conical member. A major fraction of the gas flow is withdrawn between the two conical members, by means of a pump or the like while the remaining portion, after having passed through the second conical member, is introduced into a chamber which is kept under a high vacuum and whose dimensions are sufficient to enable the free passage of the ions which are thereafter collected by the mass spectrometer where they are detected as a function of the ratio of their mass with respect to their charge. Such an apparatus, well known to the specialist in this field, is for example described in the magazine "Analytical Chemistry, Vol. 58, no. 1, Jan. 1986 pages 97 et seq".

Now experience has shown that with specimens containing high concentrations of ions of the material to be analyzed, such as silane $SiH_4$, the efficient and regular transfer of the ions up to the mass spectrometer through the two interface conical members, faces certain difficulties in view of the fact that in the plasma, the atoms (for example Si) or the ions (for example $Si+$), rapidly produce a deposit of silicon on the external surface of the conical members themselves, partially blocking the orifices of their axial ducts and thereby very substantially disturbing the analysis which is carried out through the mass spectrometer.

As a matter of fact, in the plasma which is produced, following the solution breakdown in the case of a liquid specimen, in all the cases of atomization of the molecule and excitation of the atoms, whether the specimen is liquid or gaseous, the ions and the atoms are necessarily in gaseous phase because of the temperature of the plasma (generally higher or equal to 5000° K), which is substantially higher than that of the boiling point of the substance, for example equal to 2628° K in the case of silicon. On the other hand, because of the cooling of the nickel conical members, silicon is partially solidified in contact with the latter, thus producing a deposit which is detrimental.

SUMMARY OF INVENTION

It is an object of the present invention to provide an improvement to the process of elementary analysis of a high frequency inductively coupled plasma mass spectrometer, which overcomes the disadvantage mentioned above, by limiting the plugging of the orifices of the ducts of the conical members of the apparatus, and produce a decrease of a signal produced by the mass spectrometer, which signal decrease could eventually be slightly compensated by a modification of the adjustments of the ion optics which however cannot be modified during an analysis.

For this purpose, the improvement under consideration is characterized in that it consists in adding to the specimen which is injected into the plasma a given quantity of a make-up gas, with high heat producing power, so as to raise the temperature of the plasma to locally heat the sampling conical members to prevent the deposit on the latter of the components of the specimen, which are present in the plasma.

It has indeed been observed that the temperature of the plasma produced, which depends on its electronic density and its composition, may be substantially increased by introducing in the plasma producing medium and/or the sample injected into the plasma, a supplemental input of a gas with high heat producing power, possibly improving the energy transfers between the plasma and the components of the specimen. Thus, with a plasma producing medium for example made of argon, the temperature of excitation of the plasma can thus be brought to 5000° to 7000° K, merely by adding an appropriate flow of hydrogen.

On the other hand, and according to another characteristic of the invention, the increase of the temperatures of the plasma is combined with the effect which results from an appropriate choice of the material of the conical members which are used for sampling and for sending a fraction of the specimen towards the mass spectrometer. Preferably, the material of the conical members is determined so that it presents refractory properties at high temperature and has satisfactory machining properties to produce shapes required therefor.

Advantageously, and according to a specific embodiment of the invention, the conical members are made of an alloy of niobium Nb, hafnium Hf, titanium Ti, the relative proportions of these three metallic elements being respectively in the neighborhood of 89% (Nb), 10% (Hf) and 1% (Ti).

BRIEF DESCRIPTION OF DRAWINGS

Other characteristics of a high frequency inductively coupled plasma mass spectrometer apparatus (ICP/MS), which is improved according to the invention, will further appear throughout the description which follows of an embodiment, given hereafter by way of example and without intent to limit the scope of this invention, and with reference to the annexed drawings in which.

DESCRIPTION OF PREFERRED EMBODIMENTS

Figure 1:
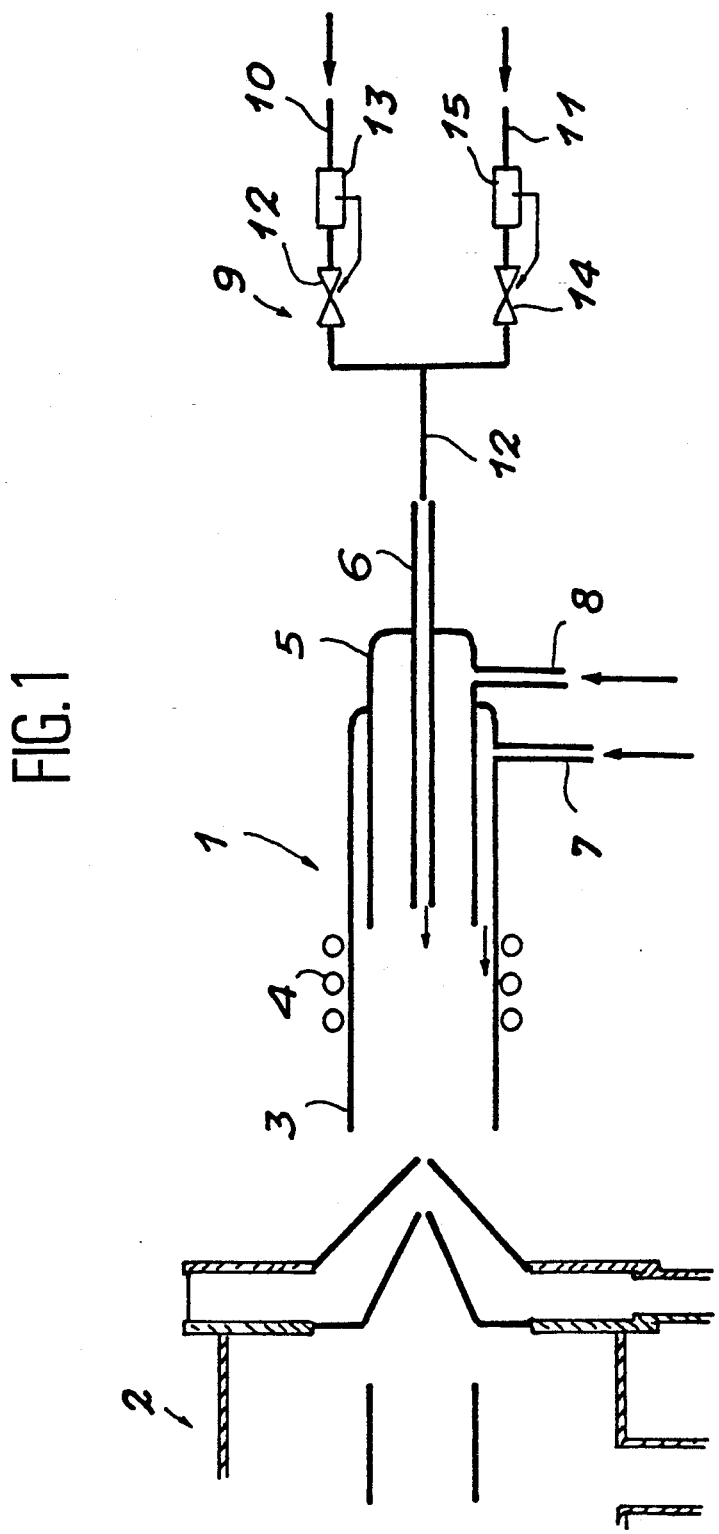
FIG. 1 is a schematic view in transverse cross-section of the apparatus under consideration.
Figure 2:
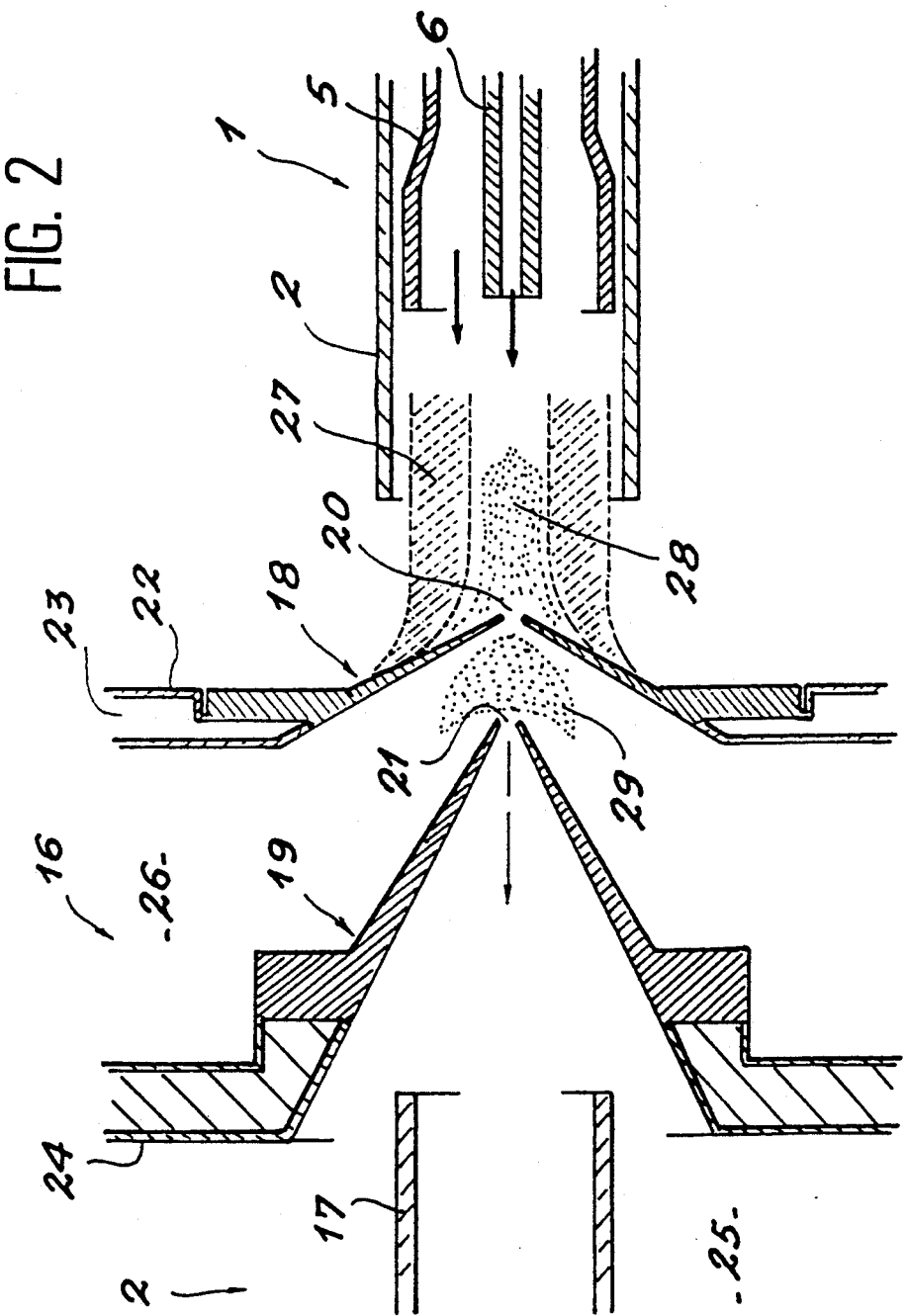
FIG. 2 is a detailed view on a higher scale of part of the apparatus, more particularly illustrating the structure of the conical members of the latter.

The apparatus represented in the drawings uses the same arrangements known in the art as the known apparatuses of the type ICP/MS, and comprises for example an injection torch 1, which is placed opposite a structure 2 for connection with a mass spectrometer, not illustrated in the drawings. The torch 1 mainly includes a tube of quartz 3 having its exterior surface associated with a high frequency induction coil 4, enabling the production of a plasma which is inductively coupled with a gaseous medium injected in the torch at an appropriate flow. Advantageously, torch 1 includes inlet means for the specimen and the plasma producing medium, which are made of a tubular member 5, concentrically disposed in the tube 3 and itself axially including an inlet duct 6. The plasma producing medium, generally argon, is introduced by means of a connection 7, between the tubular member 5 and the internal surface of the tube of quartz 3, another connection 8 also permitting to introduce, inside the tubular member 5, an auxiliary flow of another gas or the same gas as the one which constitutes the plasma producing medium, for adjusting the conditions of production of the plasma in the torch, perpendicularly to the induction coil 4. The axial duct 6 is connected to a unit 9 for introducing the specimen into the apparatus, which comprises two parallel lines respectively 10 and 11, connected together by means of a single connection line 12 with the duct 6.

The gaseous sample to be analyzed is delivered by means of line 10 through valve 12 provided with a device for the self-control and regulation of the flow 13. This specimen can be of any type and in addition can be in gaseous form or in the form of a liquid solution, the latter having previously been treated to constitute a mist of very fine droplets. In addition and according to the invention, there is introduced through the second line 11, also provided with a valve 14 and a self-control 15, an auxiliary flow of a gas with high heat producing power, preferably hydrogen, which is thus mixed with the specimen in the connection line 12 before being introduced in duct 6 in the axis of torch 1.

The specimen of gas intimately mixed with the hydrogen make-up thus supplied, is injected into the plasma, of which a portion is sampled to be sent to structure 2 for connection with the mass spectrometer, to produce a desired quantitative elementary analysis of the components of the specimen.

For this purpose, sampling of the required fraction of the specimen is carried out through an interface 16, disposed at the outlet of the torch 1 and ahead of the first electrodes 17 of the electronic optics, enabling to send this sample to the spectrometer. In known manner, the interface 16 comprises two consecutive conical members, respectively 18 and 19, coaxially mounted one behind the other, the first conical member 18 being called specimen conical member, while the latter is designated under the term sampling conical member. The conical members 18 and 19 each comprise a central orifice, respectively 20 and 21, the specimen conical member 18 having a top opening which is more substantial than that of the sampling conical member 19. Conical member 18 is unitary with a casing support 22, having an inner recess 23 enabling the circulation of a fluid for cooling the conical member, generally water. Conical member 19 is supported by a mounting structure 24 which closes a chamber 25 in which the ions sampled through the orifices 20 and 21, are treated by the electrodes 17 which accelerate them towards the spectrometer. Chamber 25 is under high vacuum. Finally, between the casing support 22 of the first conical member 18 and the mounting structure 24 of the second conical member 19 there is provided a space 26, also under vacuum but which is not as high as the one which takes place in chamber 25, this space 26 being connected to a pumping device (not illustrated). The plasma jet 27 which thus exits from torch 1 surrounds an axial zone 28, where the gaseous sample coming from the duct 6 is highly ionized; an important fraction of the sample is withdrawn towards the outside by following the surface of the first conical member 18 while the remaining portion penetrates through the orifice 20 into the space 26 where an expansion zone 29 is formed, the central part of the latter penetrating into the chamber 25 through orifice 21.

According to the invention, the addition of a gas with high heat producing power, in particular hydrogen, to the initial gas specimen, enables to raise the temperature of the plasma and thereafter to locally heat the consecutive conical members 18 and 19, for example by preventing that the orifices 20 and 21 become progressively obstructed by the deposits of the components of the sample, the temperature of these conical members being, in all cases, substantially lower than that of the plasma.

Of course, it is also suitable to choose the material of the conical members from a metal or an alloy which is capable of simultaneously be conveniently machined and to support the temperatures contemplated which can reach 7000° K. Advantageously, the conical members 18 and 19 are thus made of an alloy of niobium (89%), hafnium (10%) and titanium (1%).

There is given hereinafter a working example of the process under consideration, with a specimen of silane diluted at 1% (0.02 1/mn), which compares the results obtained with conical members of niobium-hafnium-titanium (No-Hf-Ti) with known conical members of nickel, after having added to the flow of specimen a make-up gas consisting of hydrogen. The specimen of silane is polluted with an addition of methyl iodine $CH_3I$, at very low concentration of 2 ppb/mol. The following results are obtained enabling to show the combined effect of the injection of hydrogen and the use of conical members with an alloy, which permits a limit of detection which is more performing and a higher stability of the signal characterizing the desired component (relative typical variation lower than in the case of conical members of nickel). In this example, presented in the form of a table the following parameters are used:

the injection flow is a flow of argon, enabling to carry the sample to be analyzed in the plasma (at 12 in FIG. 1). This mixture consists of argon, the gas to be analyzed and hydrogen, and the conical members are made according to the invention, of Nb-Hf-Ti.

intensity of $^{127}I$ The ions in the plasma ($Ar^+$, $Si^+$, $I^+$), once they have been sampled by the conical members, are separated in the mass spectrometer depending on the ratio of the mass with respect to the charge (m/g), then, with a detector mounted after the apparatus, the ions having the same ratio m/g are counted. The quantity of ions is thus given in the form of an intensity whose unit is the "ACPS". The measure of this intensity shows the good operation of the apparatus. A plurality of measurements were taken successively enabling to calculate a typical relative variation, of formula $$\frac{\sqrt{\sum_{i=1}^{m}(X_i - \bar{X})^2/n - 1}}{\bar{X}}$$

where $\bar{X}$ is the average of measurements $X_i$ and n is the number of these measurements.

This relative typical variation shows the reproductiveness of the measurements and the stability of the system. It may be observed that with conical members of Ni as opposed to conical members of Nb-Hf-Ti according to the invention, the system is not stable, the typical variation being of 29%. This is for example due to the formation of a deposit at the orifices of the conical members, thus modifying the jet of ions at the inlet of the mass spectrometer. On the other hand, in the case of conical members of Nb-Hf-Ti, the relative typical variation is of 1.5% only, thus establishing the gain of stability of the signal.

The deposits formed at the openings of the conical members are also the main reason for the low content of the mean intensity of the ion $^{127}I$ in the case of conical members of Ni. In the case of conical members of alloy according to the invention, a gain of a factor of 5 is obtained with respect to the intensity of the ion $^{127}I$, found with conical members of nickel.

The consequence of these two effects (increase of the average intensity and better stability of the signal) thus enables to obtain a better detection limit and a lower detection of the content of impurities in the gas to be analyzed.

|  | Conical members Ni | Conical members Nb—Hf—Ti |
|---|---|---|
| Injection flow | 0.7 1/mn | 0.7 1/mn |
| Diluted $H_2$ flow 5% in argon | 0 | 0.15 1/mn |
| Ar flow, $SiH_4$ | 0.7 1/mn | 0.55 1/mn |
| average intensity of $^{127}I$ | 6 700 ACPS(1) | 32 900 ACPS |
| Relative typical variation of the intensity of the signal $^{127}I$ | 29% | 1.5% |
| Intensity of bottom measured with respect to the mass $^{125}Te$ | 20 ACPS | 15 ACPS |
| Typical variation of the bottom with respect to the mass $^{125}Te$ | 1.75 ACPS | 1.1 ACPS |
| Detection limit of $^{127}I(2)$ | 5 ppb/a | 0.7 ppb/a |

(1)Area Counts Per Second
(2)Detection limit according to the definition of the norm of IUPAC, 1987, equal to 3 $\sigma.c/I$ where $\sigma$ is the typical variation of the bottom, c the concentration of the impurity injected with respect to the sample to be analyzed and I the mean intensity of the withdrawn impurity.

We claim:

1. In a process for the elementary analysis of a specimen by high frequency inductively coupled plasma mass spectrometry, by means of an apparatus including a torch for producing plasma from a plasma producing medium and for injecting said specimen in said plasma, and an interface for taking a sample in said specimen, comprising two consecutive conical members disposed along the same axis except that said conical members have angles with different apices and are each provided with an axial orifice enabling a fraction of the specimen to be analyzed to pass therethrough, the improvement which comprises adding a given quantity of make-up gas to the specimen which is injected into the plasma, said make-up gas having a high heat producing power, so as to raise the temperature of the plasma for locally heating the sampling conical members thereby preventing the components of the specimen which are present in the plasma from depositing on said conical members.

2. The process according to claim 1, wherein the high heat producing power gas consists of hydrogen.

3. The process according to claim 1, which comprises bringing the temperature of the plasma to about 7000° K, and wherein the plasma producing medium permitting the production of said plasma consists of argon.

4. An apparatus for taking a sample enabling to carry out the process according to claim 1, including sampling conical members made of material having refractory properties at high temperature and a good machinability.

5. The apparatus according to claim 4, wherein the conical members are made of a material consisting of an alloy of niobium (Nb), hafnium (Hf), titanium (Ti).

6. The apparatus according to claim 5, wherein the components of the alloy are in the ratios 89% Nb, 10 Hf and 1% Ti.

* * * * *